(12) United States Patent
Roeck et al.

(10) Patent No.: US 11,647,950 B2
(45) Date of Patent: May 16, 2023

(54) HEARING DEVICE WITH OPTICAL SENSOR AT SPOUT

(71) Applicant: Sonova AG, Stafa (CH)

(72) Inventors: Hans-Ueli Roeck, Hombrechtikon (CH); Christian Frei-Krumme, Stafa (CH); Konstantin Silberzahn, Meilen (CH); Markus Muller, Mannedorf (CH); Markus Leuthold, Stafa (CH)

(73) Assignee: SONOVA AG, Stäfa (CH)

( * ) Notice: Subject to any disclaimer, the term of this patent is extended or adjusted under 35 U.S.C. 154(b) by 475 days.

(21) Appl. No.: 16/834,252

(22) Filed: Mar. 30, 2020

(65) Prior Publication Data

US 2021/0298670 A1     Sep. 30, 2021

(51) Int. Cl.
| | |
|---|---|
| A61B 5/00 | (2006.01) |
| A61B 5/026 | (2006.01) |
| A61B 5/0295 | (2006.01) |
| H04R 25/00 | (2006.01) |

(52) U.S. Cl.
CPC .......... *A61B 5/6803* (2013.01); *A61B 5/0261* (2013.01); *A61B 5/0295* (2013.01); *A61B 5/6817* (2013.01); *H04R 25/40* (2013.01); *A61B 2562/0238* (2013.01); *A61B 2562/185* (2013.01)

(58) Field of Classification Search
CPC ... A61B 5/6803; A61B 5/0261; A61B 5/0295; A61B 5/6817; A61B 2562/0238; A61B 2562/185; A61B 5/02416; A61B 5/6816; H04R 25/40; H04R 25/60; H04R 2225/023; H04R 2225/025; H04R 25/305; H04R 2225/41; G01J 1/44; G01J 2001/446
See application file for complete search history.

(56) References Cited

U.S. PATENT DOCUMENTS

| | | | |
|---|---|---|---|
| 6,556,852 B1 * | 4/2003 | Schulze | A61B 5/01 |
| | | | 600/323 |
| 2019/0082974 A1 | 3/2019 | LeBoeuf et al. | |
| 2019/0230428 A1 | 7/2019 | Austen | |

(Continued)

OTHER PUBLICATIONS

Eric S. Winokur, David Da He, Charles G. Sodini, "A Wearable Vital Signs Monitor at the Ear for Continuous Heart Rate and Pulse Transit Time Measurements", Sep. 2012, Annual International Conference of the IEEE Engineering in Medicine and Biology Society (Year: 2012).*

(Continued)

*Primary Examiner* — Eric F Winakur
*Assistant Examiner* — Abid A Mustansir
(74) *Attorney, Agent, or Firm* — Pearne & Gordon LLP

(57) ABSTRACT

An in-ear hearing device includes a light source configured to emit light, a photodetector configured to detect the emitted light after the emitted light passes through tissue of a subject, a spout; an audio receiver configured to deliver a sound to the subject through the spout, and a dome configured to conform to a shape of a subject's ear canal when the hearing device is in the ear canal. An output of the light source and an input of the photodetector are separated by the dome, and the dome absorbs and/or reflects at least part of the emitted light. The photodetector may be a forward biased photodiode. The sensor device can be realized with power levels, circuitry components, and in package sizes, of hearing devices.

19 Claims, 10 Drawing Sheets

(56) References Cited

U.S. PATENT DOCUMENTS

| | | | |
|---|---|---|---|
| 2020/0085326 A1* | 3/2020 | Fransen | H04R 25/60 |
| 2021/0168539 A1* | 6/2021 | Stephenson | A61B 5/0205 |
| 2021/0298619 A1* | 9/2021 | Stephenson | A61B 5/02416 |

OTHER PUBLICATIONS

Search Report issued in European Patent Application No. 21165633.5 dated Aug. 11, 2021.

* cited by examiner

HEARING DEVICE WITH OPTICAL SENSOR AT SPOUT

BACKGROUND

Optical sensors use a light source to emit light into an environment and a photodetector to detect light from the environment in order to obtain information about the environment. For instance, optical sensors of that kind are often employed to project light into tissue (e.g., skin) of a subject and to measure reflected or transmitted light characteristics of the projected light. The detected light intensity varies as a function of blood flow through the vasculature throw which the light passes. Thus, the measured intensity signal over time represents a photoplethysmogram (PPG) signal, which can be processed to determine heart rate, blood pressure, and other physiological properties.

Although there are many places on the body where data can be gathered (e.g., where blood vessel density and tissue type and thickness are optimal for optical transmission and reflectance), some are more prone to effects of noise caused by movement and by ambient light from the environment. Additional factors that can affect quality of PPG signals include the measurement location, wavelength of emitted light, body movement, light from the environment, and skin color of the subject. Still further, PPG sensors having different materials that may be transparent and or reflective to the emitted light (including infrared and other types of (in)visible light wavelengths) can cause interferences with the resulting sensor data. Considering this, many PPG sensor form factors utilize contact optical sensors where the light source and detector are in contact with the skin. This helps prevent the leakage of emitted light and the bleeding of light from the environment into the detector, thus reducing noise caused by ambient light.

Some PPG sensors are designed to take measurements at a subject's ear. When the PPG sensor is part of a standard "receiver-in-the-canal" (RIC) hearing device module (one without shells customized to the shape of a subject's ear canal), the PPG sensor does not touch the wall of the ear canal. For standard hearing devices, there is not sufficient optical isolation between the photodetector and the light source, which can result in a short-circuit between the light source and the photodetector. Accordingly, the user of a standard hearing device can suffer from unreliable measurements of the PPG sensor.

The larger the distance between the light source and the photodetector, the greater the probability that the detected light has passed through vasculature in the tissue and thus the greater probability that an acceptable physiological signal can be extracted from the detected light signal. However, such long paths greatly attenuate the light emitted by the light source. As a result, either a strong and power consuming light source and/or sophisticated amplification circuitry is required to extract an acceptable physiological signal. Such power is greater than that generally used in hearing devices, and the requisite electrical components for power control and amplification increase the PPG sensor system complexity and can generate electrical interference in small packages like those associated with hearing devices. When multiple light sources, potentially with different wavelengths, are used by the PPG sensor, complexity of the sensor system is also increased.

BRIEF SUMMARY OF THE INVENTION

According to an example of the present disclosure, an optical sensor device/hearing device comprises a light source configured to emit light; a photodetector configured to detect the emitted light after interacting with tissue of a subject; a spout; an audio receiver configured to deliver a sound to the subject through the spout; and a dome configured to conform to a shape of a subject's ear canal when the hearing device is in the ear canal, wherein the dome absorbs and/or reflects at least part of the emitted light, and wherein an output of the light source and an input of the photodetector are separated by the dome. In some instances, a reliability of measurements of the hearing device may be improved by separating the output of the light source and the input of the photodetector by the dome. In some implementations, the light source comprises at least one light emitting diode.

The light source may be configured to emit directional light toward a wall of the ear canal. The light source may be configured to emit diffuse light within the ear canal. The light source may be located at the spout and the input of the photodetector may be located at the receiver. The output of the light source may be located at the receiver and the input of the photodetector may be located at the spout. The spout may be transparent to a wavelength of the emitted light. The spout may comprise a light guide connected to the input of the photodetector. The light guide may comprise a waveguide configured to guide light with a wavelength of the emitted light.

The output of the light source may be at a discrete location from the light source, the output of the light source being connected to the light source via a light guide. The input of the photodetector may be at a discrete location from the photodetector, the input of the photodetector being connected to the photodetector via a light guide. The output of the light source may be located at the spout and the input of the photodetector may be located at the receiver, wherein the output of the light source may be at a discrete location from the light source, the output of the light source being connected to the light source via a first light guide, wherein the input of the photodetector may be at a discrete location from the photodetector, the input of the photodetector being connected to the photodetector via a second light guide. The output of the light source may be located at the receiver and the input of the photodetector may be located at the spout, wherein the dome may be further opaque to ambient light.

The optical sensor may further comprise a shield opaque to wavelengths of ambient and visible light, and configured to shield the photodetector from the wavelengths of ambient and visible light. The output of the light source and the input of the photodetector may be preferably at least at a 45° angle when viewed in a parasagittal cross-section of the ear canal. The angle may be acute relative to a posterior wall of the ear canal. The light source may be configured to emit light having a wavelength in the near infrared region. For instance, the light source may be configured to emit light having a wavelength of 800 nm and/or 850 nm and/or 880 nm and/or 904 nm and/or 910 nm and/or 940 nm and/or 950 nm. The wavelength in the near infrared region may be a first wavelength and the light source may be configured to emit light having a second wavelength of about 660 nm.

The dome may be configured to contact a tissue of the ear canal and to absorb and/or reflect at least part of the emitted light such that an intensity of the emitted light with a wavelength passing through the dome is smaller than an intensity of the emitted light with the wavelength passing through the tissue. In some instances, the dome may absorb and/or reflect at least part of the emitted light such that an intensity of the emitted light passing through the dome is smaller than an intensity of the emitted light passing through the tissue. In some instances, the dome may be opaque to a wavelength of the emitted light. In some instances, the dome may be opaque to the emitted light.

The photodetector may comprise a forward biased photodiode, and the optical sensor device/hearing device may be configured to determine an intensity of light detected by the photodetector by measuring a time delay between an onset of a forward voltage of the photodetector and an onset of a forward current of the photodetector. In some instances, the light source is configured to emit light with a light intensity such that the time delay is at least 200 ns.

DETAILED DESCRIPTION OF THE INVENTION

Considering the above, the present disclosure relates to a hearing device having a PPG sensor that overcomes the above-described deficiencies. Such a hearing device may be a receiver-in-the-canal (MC) device comprising a "behind-the-ear" part (or "BTE" part) configured to be worn behind the ear and a sound delivery system (SDS) part configured to be worn at least partially in the ear (ITE). The hearing device may also be only an ITE hearing device configured to be worn at least partially in the ear canal or a completely-in-the-canal (CIC) hearing device configured to be worn completely in the ear canal, each provided without a BTE part.

Figure 1:
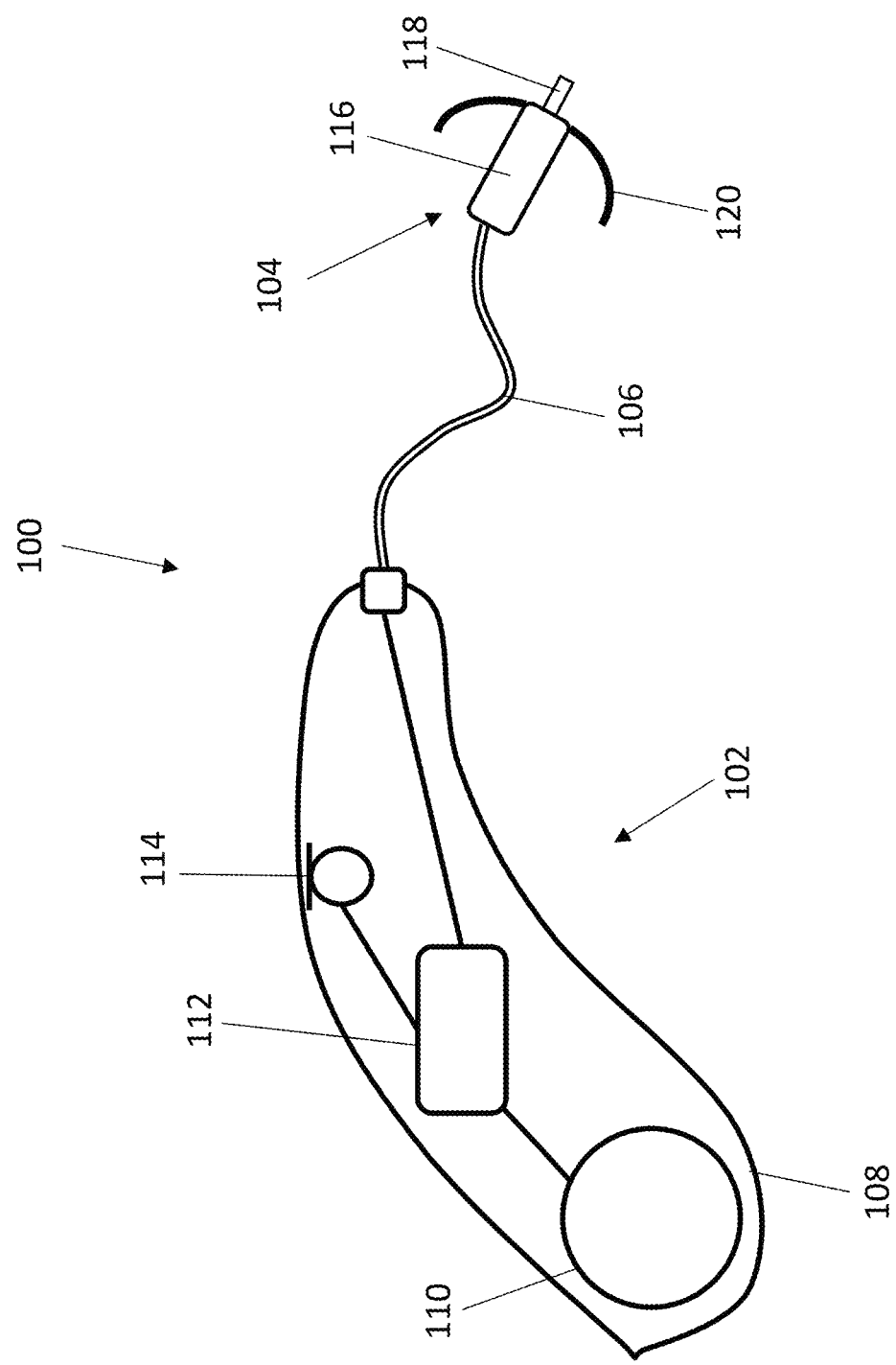
FIG. 1 illustrates an example receiver-in-the-canal (RIC) hearing device.

An example MC hearing device 100 is illustrated in FIG. 1. The RIC device 100 therein comprises a BTE part 102 and an SDS part 104 connected by a cable 106. The cable 106 may be an electric cable or an air conduction cable. The BTE part 102 comprises a housing 108 for a battery 110, processor 112, and microphone 114. The SDS part comprises a receiver 116, a spout 118, and a dome 120.

The BTE part 102 is configured to collect sound at the microphone 114, process the collected sound with the processor 112, and deliver the processed sound to the receiver 116 of the SDS part 104 via cable 106. The receiver 116 may comprise a loudspeaker configured to generate an audible version of the processed sound, and a printed circuit board (PCB) on which electronic components for sound generation are provided. The spout 118 may be particularly configured to deliver the sound output by the loudspeaker toward the tympanic membrane inside the ear canal by having a tubular shape with an opening facing the eardrum. The dome 120 may be elastic, or the like, such that it is configured to adjust its shape to the ear canal, thereby supporting the receiver 116 within the ear canal.

In other embodiments, the loudspeaker may be part of the BTE part 102. In these cases, the cable 106 may be an air conduction cable configured to deliver the output sound to the spout. In still other embodiments, the microphone 114, processor 112, and battery 110 may be wholly contained within the SDS part 104, as with ITE only and CIC hearing devices, such that the BTE part 102 is not provided.

Figure 2:
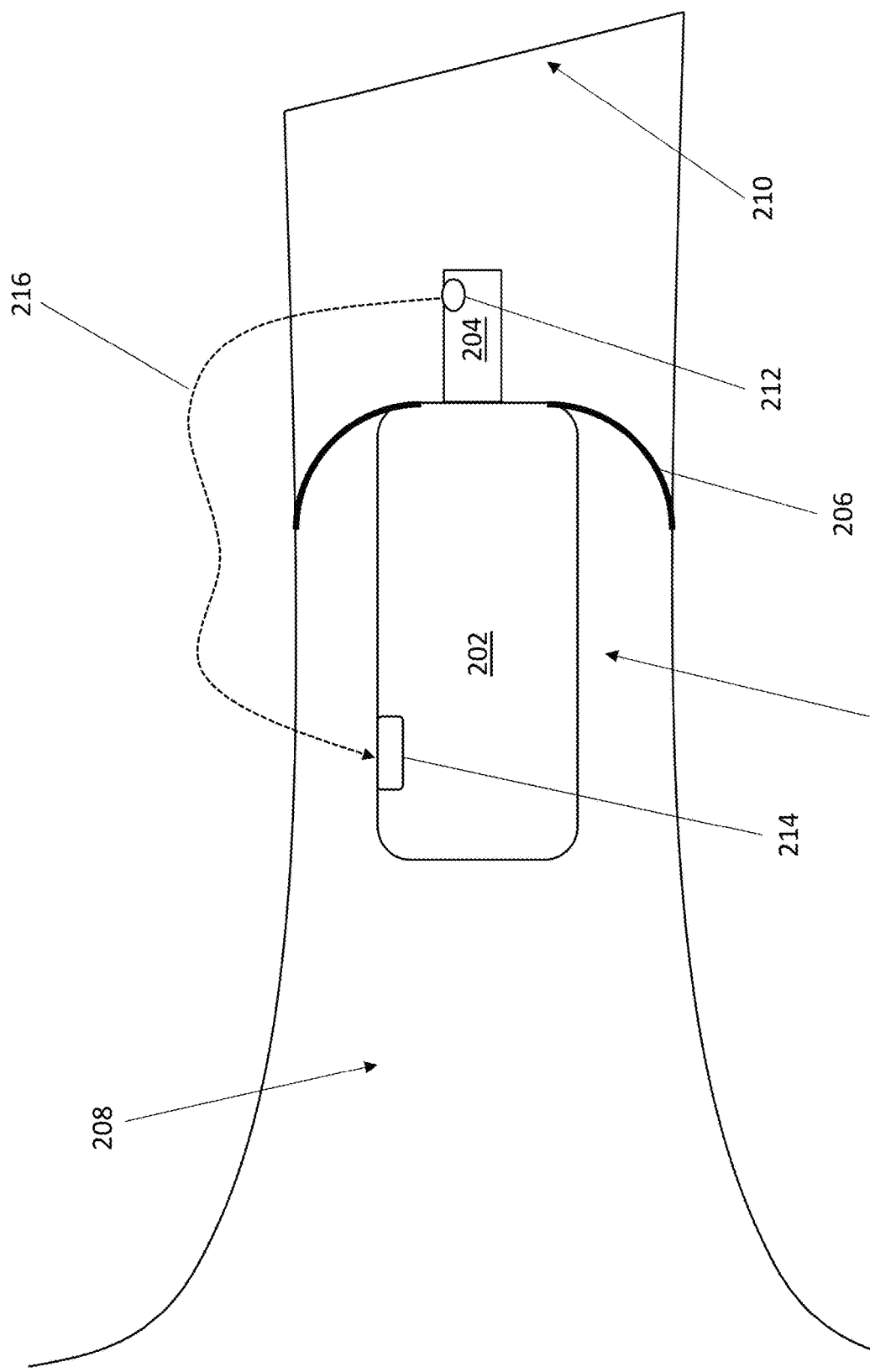
FIG. 2 illustrates an example sound delivery system (SDS) part of a RIC hearing device having a PPG sensor in an ear canal.

Turning to FIG. 2, the general operation of a PPG sensor with an ITE part of a hearing device is illustrated. As shown therein, an example ITE part 200 (having a receiver 202, spout 204, and dome 206) is located in an ear canal 208 with the spout end of the ITE part 200 closest to the tympanic membrane 202. Here, the ITE part 200 may be said to be divided into a medial half (that closest to the tympanic membrane 202) and a lateral half (that closest to the opening of the ear canal). Although the figure illustrates the SDS part completely in the canal 208, it is again noted that the present disclosure is also applicable to hearing devices that are only partially inserted into an ear canal.

According to one embodiment, illustrated in FIG. 2, a light source (e.g., an LED or OLED) 212 is provided in the medial half of the SDS part 200 (shown at the spout 204), and a photodetector 214 is provided in the lateral half of the SDS part 200 (shown at the receiver 202). The light source 212 is configured to emit light 216 through the wall of the ear canal 208, where it passes through vasculature; and the photodetector 214 is configured to detect the emitted light 216 that re-enters the ear canal 208. The light source 212 may emit any wavelength of light, e.g. green or red or infrared. In one embodiment, the wavelength may be in the near infrared spectrum, which may comprise a wavelength between 780 nm and 2500 nm. Such a wavelength can be less prevalent in many ambient light sources such as sunlight. In some instances, at least one wavelength of the emitted light is 800 nm and/or 850 nm and/or 880 nm and/or 904 nm and/or 910 nm and/or 940 nm and/or 950 nm. In some instances, at least one wavelength of the emitted light is in the red spectrum, e.g. 660 nm. In some instances, at least one wavelength of the emitted light is in the green spectrum, e.g. 520 nm.

Light source 212 may also be configured to emit light having at least two different wavelengths. For instance, light source 212 may comprise at least two light emitters each configured to emit light having a respective wavelength and/or a plurality of wavelengths. In some instances, a first wavelength of the emitted light is in the near infrared spectrum, for instance at least one of 800 nm and/or 850 nm and/or 880 nm and/or 904 nm and/or 910 nm and/or 940 nm and/or 950 nm, and a second wavelength of the emitted light is 660 nm. Such a wavelength combination may be advantageously applied, for instance, to determine a peripheral capillary oxygen saturation value in the tissue. The dome 206 is preferably predominantly opaque to at least one wavelength of light emitted by the light source 212 and/or wavelengths of visible ambient light, which predominantly means that the light intensity at said wavelength passing through the dome is significantly smaller than the light at said wavelength passing through the tissue to the photodetector. When blocking wavelengths of light emitted by the light source 212, the dome 204 thus optically isolates the light source 212 and photodetector 214, thereby preventing the emitted light 216 from traveling directly to the photodetector 214 without first passing through the tissue surrounding the ear canal 208. For that purpose, the dome 206 might be of any suitable material and/or might contain one or multiple layers and/or coatings to achieve the desired opaqueness.

Locating the light source 212 and photodetector 214 at different positions of the SDS part 200 as shown in FIG. 2 mitigates interference that can lead to low quality data measurement. This is in contrast to current designs in which the light emitter and photodetector are provided on a single PCB in the receiver 202. Further, the separation causes the emitted light 216 to travel farther through the human skin, thus providing the greatest opportunity for it to pass through vasculature and provide relevant information. At least part of the emitted light 216 is scattered and/or reflected multiple times inside the tissue. Another part of the emitted light 216 may be absorbed by the tissue. After interacting with the tissue, at least part of the emitted light 216 can be detected by photodetector 214.

As shown in FIG. 2, the light source 212 is a single LED or OLED mounted directly into the spout 204. However, the light source 212 may be implemented in any manner to achieve a desired output characteristic. For example, the light source 212 may be mounted directly into the spout 204 (e.g., emitting light through a window, opening, or the like of the spout 204), or be mounted externally on the spout 204. In other examples, the light source may be at a distance from the end of the spout 204 such that any emitted light is guided to an output location at the spout 204 by a light guide such as an optical fiber. Similarly, the light source 212 could instead be integrated in the body of a loudspeaker and emit light through the sound outlet of the loudspeaker. The light source 212 may be configured to directionally output light toward the eardrum, or toward the wall of the ear canal; or be configured to emit diffuse light that lights up the ear canal as widely as possible.

Figure 3B:
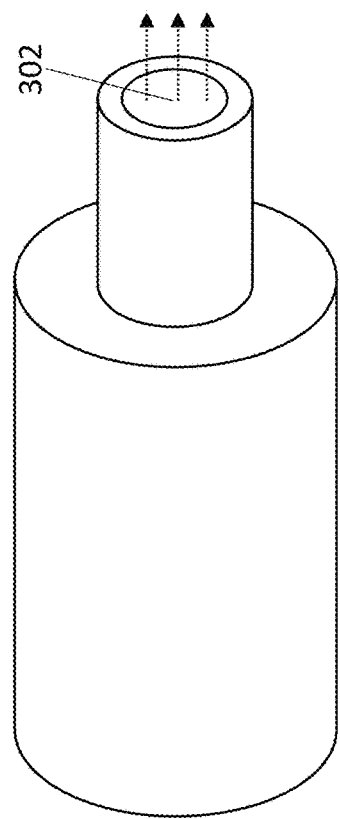
FIGS. 3A, 3B, 3C, 3D, and 3E illustrate example light source outputs from an ITE part of a hearing device.
Figure 3D:
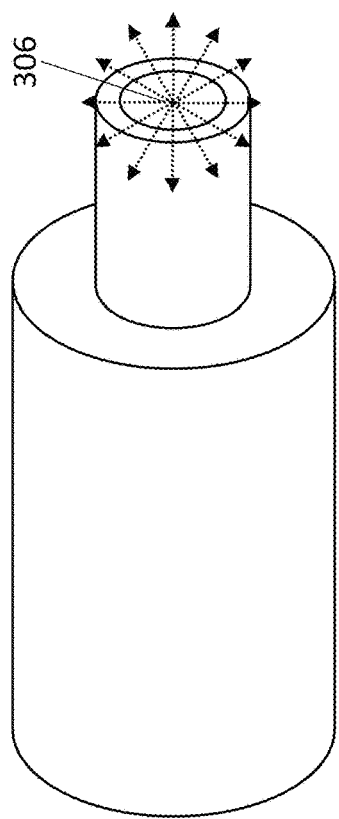
Figure 3A:
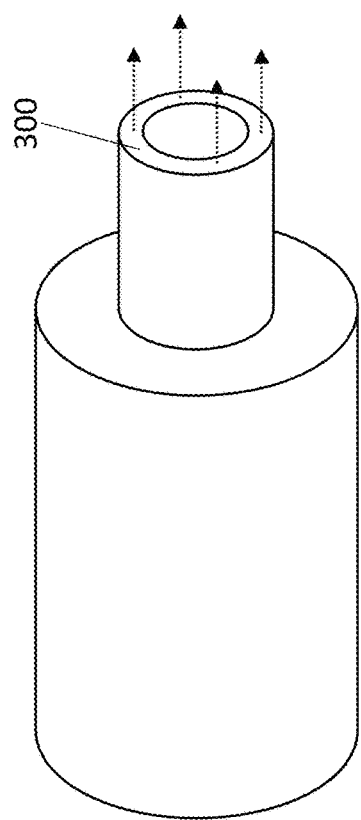
Figure 3C:
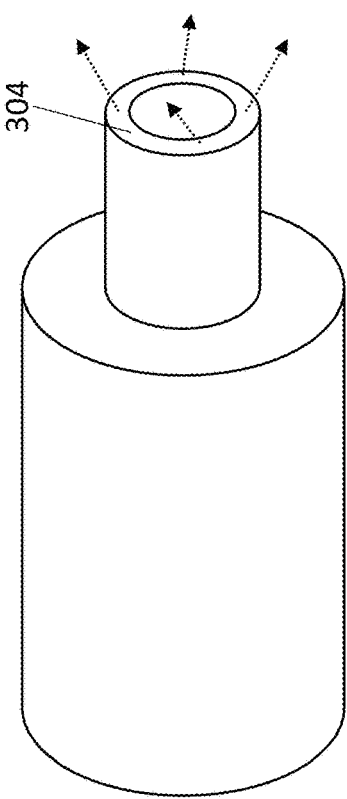
Figure 3E:
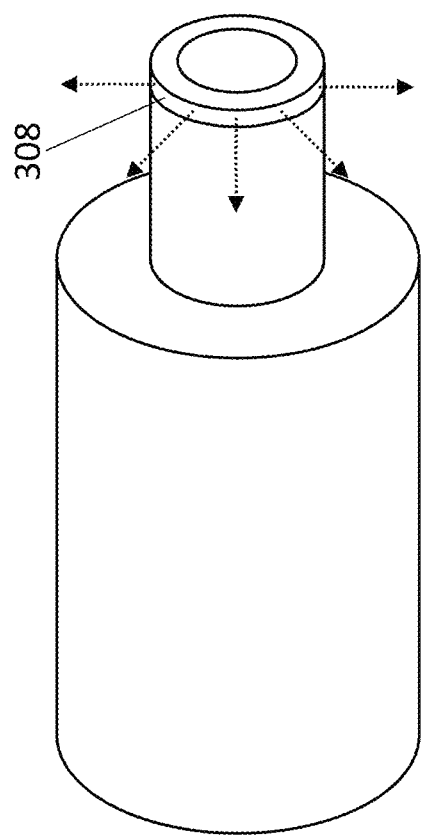

Examples of various light outputs and light source configurations are illustrated in FIGS. 3A-3E. More particularly, FIG. 3A illustrates light directionally output toward an eardrum from a light source 300 located end of the spout. The light source 300 may take the shape (a ring) of the spout as shown in FIG. 3A, or be a discrete point (or plurality of point) light source(s) located at the end of the spout. Similarly, FIG. 3B illustrates directional output of light toward the ear drum through an opening 302 of the spout, through which the output of loudspeaker is provided. In such an instance, the light source may be within the opening, or as noted above, be integrated with the loudspeaker. Similar to FIG. 3A, FIG. 3C illustrates a diffuse light emitted by a ring-shaped light source 304 at the end of the spout. Again, the light source may also be embodied as a single, or plurality of, discrete point light source(s). FIG. 3D illustrates such a diffuse light emitted from an opening of the spout 306, where the light source may be embodied as described with respect to FIG. 3B. Finally, FIG. 3E illustrates yet another directional light source 308 embodied in a ring shape (either as a single light source or one or more discrete point light sources) around a side of the spout. According to this configuration, the light is directionally emitted toward a wall of the ear canal. Such a configuration of a light source may also be emit a diffuse light around the spout toward the wall of the ear canal.

Similar to the above descriptions of light sources, the photodetector 214 may be configured to directionally receive light from the ear canal wall, or to detect scattered light from any direction. The photodetector 214 may also be located within the receiver 202, and thus detect the emitted light 216 through a window, opening or like in the receiver 202, or be mounted externally to the receiver 202. Still in other embodiments, the photodetector 214 may be located within the receiver 202, away from its housing, or at any other part of the hearing device. In such configurations, the emitted light 216 may be collected at an input location discrete from the light source 212, and guided via a light guide to the photodetector 212. In any of these variations, a shield opaque to wavelengths of ambient and visible light (e.g., embodied as a window) may cover an input to the photodetector 214. Such a shield reduces ambient light detected by the photodetector 214, thereby reducing the needed intensity of light emitted by the light source 212 and the required power for the light source 212. The shield might also be a narrowband filter, passing only the narrow wavelengths of the LED light source but no other visible or invisible light. Further, complex circuitry for removing noise induced by detected ambient light can also be minimized, thereby simplifying the device. This can also increase quality of measurements from the photodetector 214.

Figure 4:
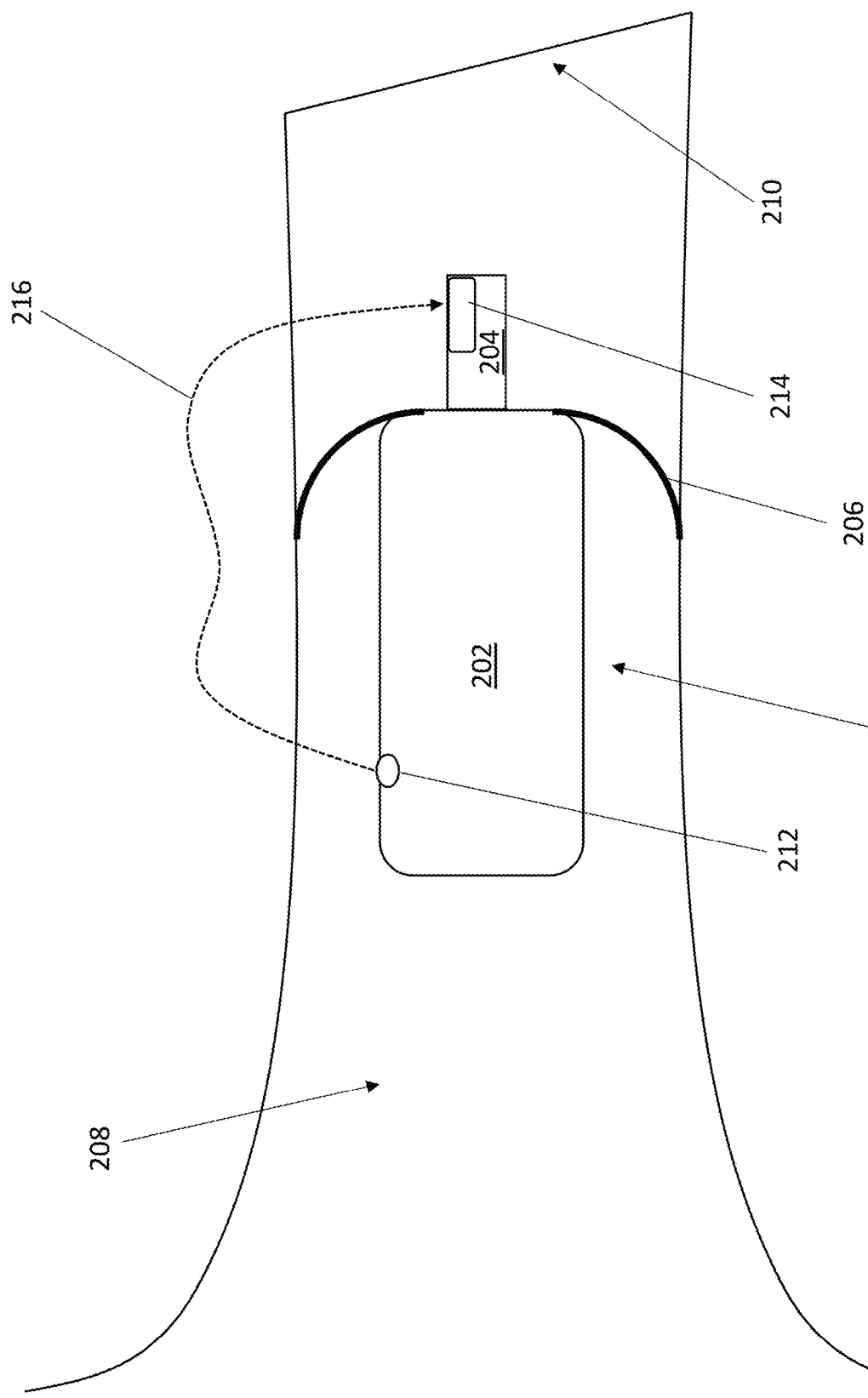
FIG. 4 illustrates a further example of an SDS part having a PPG sensor in an ear canal.

According to another embodiment, as illustrated in FIG. 4, the locations of the light source 212 and the photodetector 214 may be reversed such that the photodetector 214 is located at the medial half of the SDS part 200, for example at the spout 204; and the light source 212 is located at the lateral half of the SDS part 200, for example at the receiver 202. In such a case, the dome 206 can thus again serve to limit direct detection of emitted light at the photodetector 214. As noted above, measurement quality from the photodetector 214 can be improved by reducing the detected ambient light because deeper portions of the ear canal are darker, particularly when the dome 206 is present. Accordingly again, a lower intensity light source requiring less operating power may be utilized.

Figure 5:
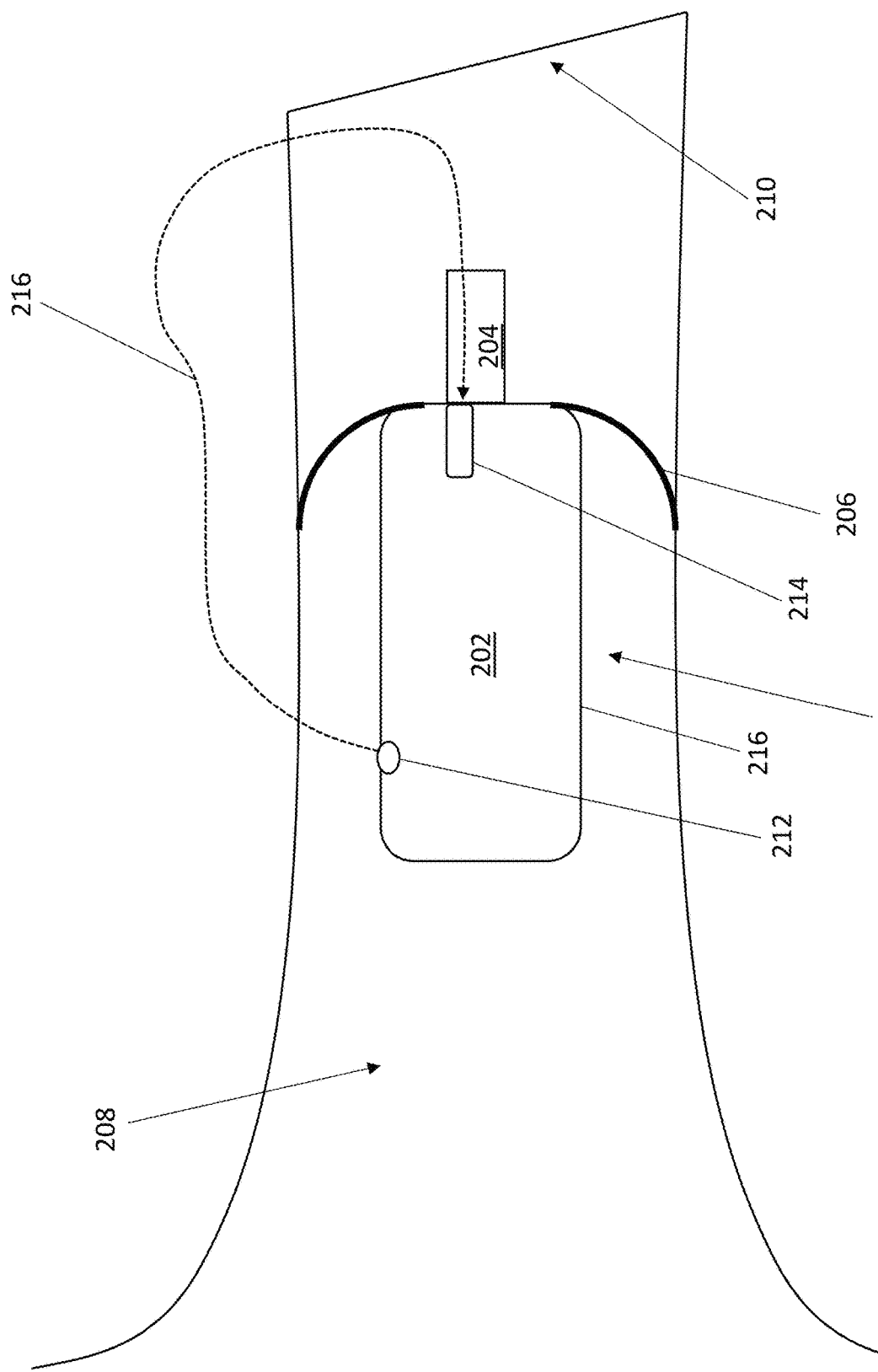
FIG. 5 illustrates a further example of an SDS part having a PPG sensor in an ear canal.
Figure 6:
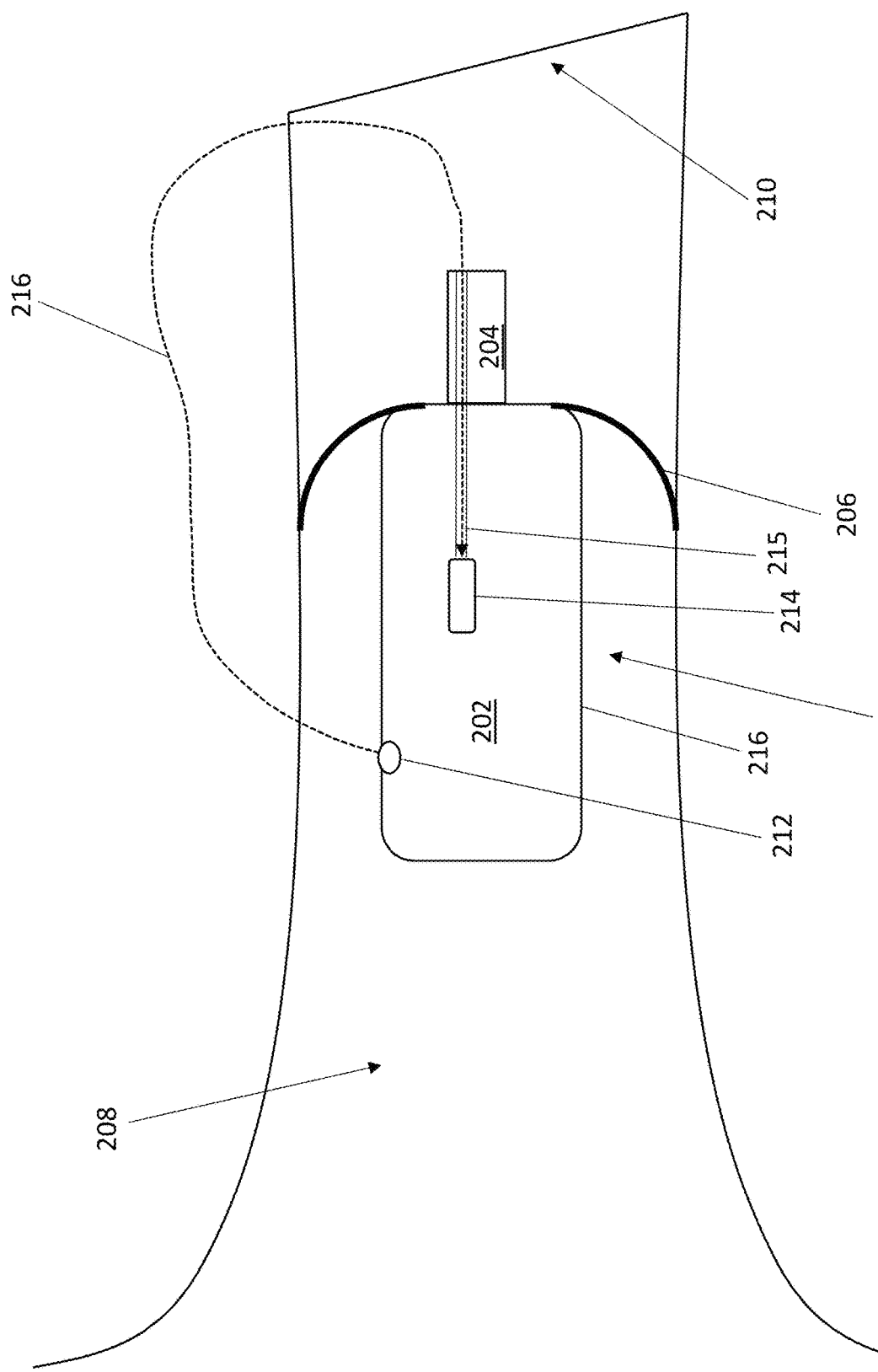
FIG. 6 illustrates a further example of an SDS part having a PPG sensor in an ear canal.

According to other embodiments, as illustrated in FIGS. 5 and 6, the photodetector 214 is located inside the receiver 202. For instance, receiver 202 may comprise a housing 216 and photodetector 214 is located inside an inner volume enclosed by the housing 216 of receiver 202. It may be that the input of photodetector 214 is in optical communication with the spout 204. For example, the input of photodetector 214 may be connected to the spout 204. In some instances, as illustrated in FIG. 5, the input of photodetector 214 may be located at a lateral end of the spout 204 leading to the inner volume enclosed by the housing 216 of receiver 202. The spout 204 may be transparent to at least one wavelength of the light emitted by light source 212. In particular, the spout 204 may comprise a portion configured as a light guide allowing the emitted light 216 to travel between an outer surface of the spout 204, for instance a surface at the medial end of the spout 204, and the lateral end of spout 204. In some instances, as illustrated in FIG. 6, the spout 204 may comprise a light guide 215 extending through a part of the inner volume enclosed by the housing 216 of receiver 202. For example, the light guide 215 may extend between the medial end of the spout 204 and the input of photodetector 214. The light guide 215 may comprise a waveguide, for instance an optical fiber and/or a dielectric waveguide transparent for at least one wavelength of the emitted light. The emitted light 216 may thus be detected by the photodetector 214 inside the receiver 202.

In still other examples, a light source could be provided at the BTE part of the hearing device. In such variations, the light may be guided to, and emitted from, any location of the SDS part via a light guide.

Figure 7:
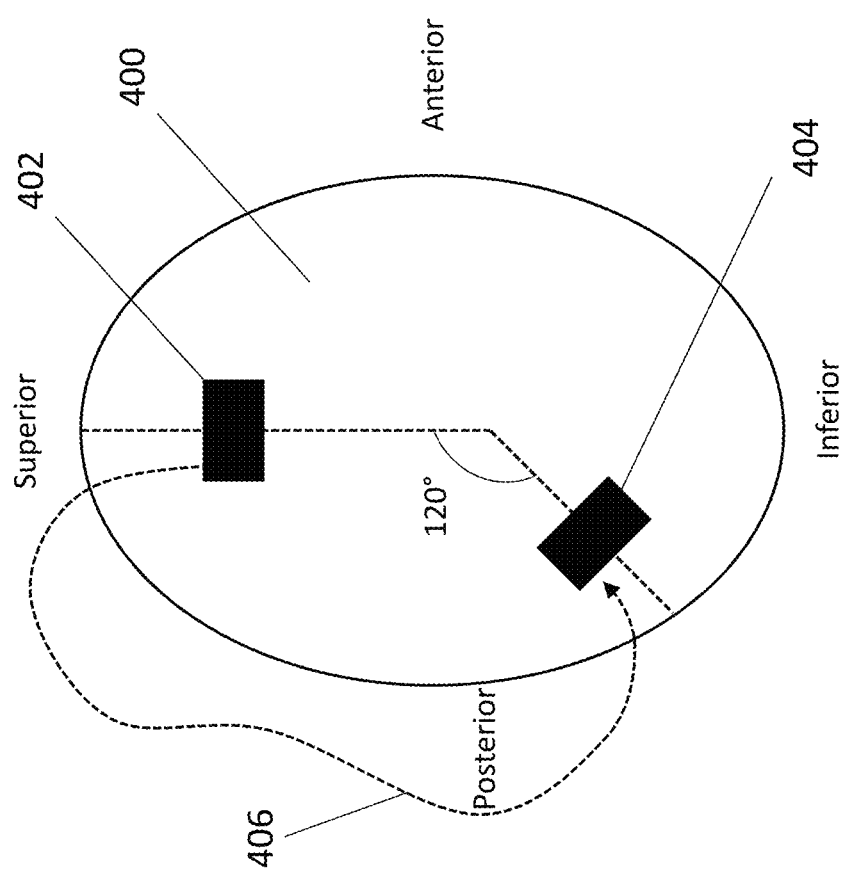
FIG. 7 illustrates a cross-section of a right ear canal showing the relative angles of a light source and photodetector of a PPG sensor of a hearing device therein.

Regardless of the relative locations of a light source and photodetector, the output of the light source in the ear canal (or its wall) and the input to the photodetector are preferably at least at a 45° angle, and more preferably at an angle greater than 90° and up to and including 180°, when viewed in a parasagittal cross-section of the ear canal. An example cross-section of a right ear canal is shown in FIG. 7 to illustrate this concept. As seen therein, a light source 402 and a photodetector 404 in an ear canal 400 are at angle of approximately 120°. Such an angle helps maximize a distance traveled by the light 406 emitted by the light source 402 prior to detection at the photodetector 404. It is also possible to maximize the distance traveled by the light 406 by maximizing the linear distance between the light source 402 and the photodetector 404. For example, placing the light source 402 at a medial-most location of the SDS part, and the photodetector 404 at a lateral-most location of the ITE part provides a greater travel distance of light 406 than when the light source 402 and photodetector 404 are placed relatively close to each other.

Still further, as movement of the ear canal wall due to jaw movement is most dominant on the anterior wall, the light path 406 is preferably tailored to be within the posterior ear canal wall, as is shown in FIG. 7, to mitigate jaw movement artifacts. In other words, the angle between the light source 402 and the photodetector 404 is acute relative to the posterior wall of the ear canal. If however the jaw movements are intended to be detected, then the light path 406 may be tailored to predominantly pass through the anterior wall. The tailoring of the light path 406 may be accomplished by directional light output from the light source 402 as discussed, directional detection of light at the photodetector 404 as also discussed above, and/or by adjusting the angle between the light source 402 and photodetector 404. In a further embodiment, different light sources or photodetectors might cover in combination different light paths, one being intentionally sensitive to jaw movements and another not predominantly not.

In some embodiments, the photodetector may be a reverse biased photodiode, in which an incident light induces a current proportional to the intensity of the incident light. Thus, measured current of the photodiode can indicate the intensity of detected light. However, other embodiments may utilize a forward biased photodiode by measuring a time delay between applying a forward voltage and a change in the respective forward current of the photodiode, which is dependent upon the incident light intensity.

Figure 8B:
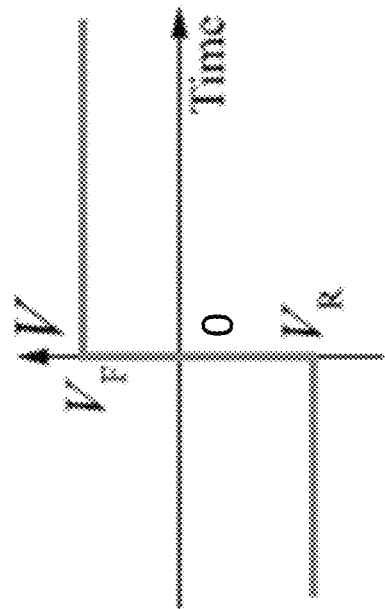
FIGS. 8A, 8B, and 8C illustrate operating characteristics of a forward biased photodiode.
Figure 8C:
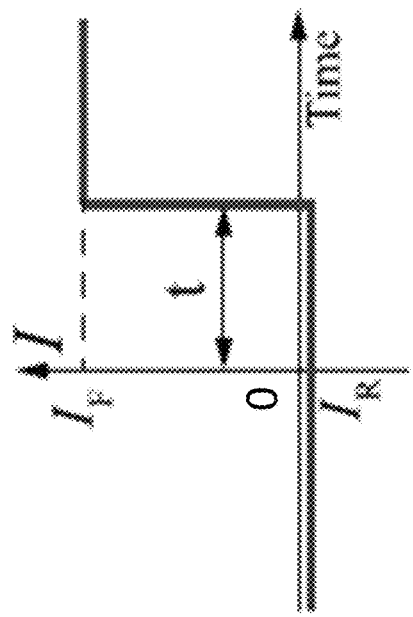
Figure 8A:
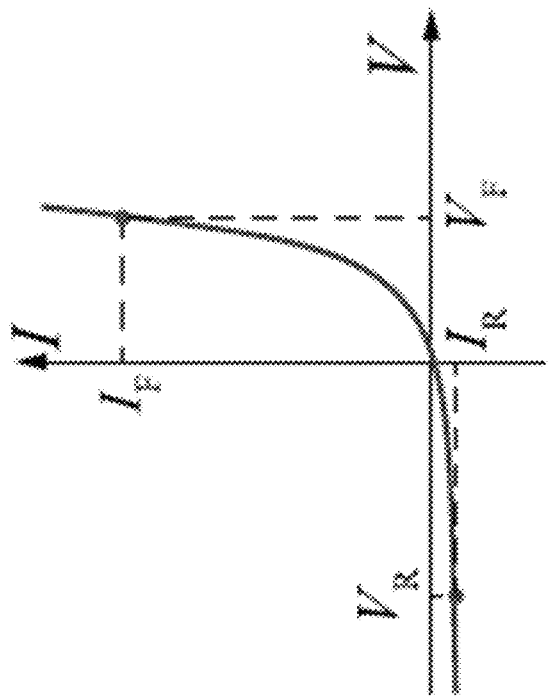

As shown in FIGS. 8A-C, this time is dependent upon the intensity of incident light at the photodiode, whereby the change in forward current takes longer for lower light intensities than for higher light intensities. More particularly, FIG. 8A illustrates an I-V curve for an example forward-biased photodiode. IF and VF correspond to the forward current and voltage, respectively; and IR and VR correspond to the reverse current and voltage, respectively. Comparing FIGS. 8B and 8C, it is seen that if the forward voltage VF is applied at a time zero, the current does not increase to the forward current IF until a time t. This time t is inversely proportional to the intensity of light, where lower intensity light corresponds to a longer time t.

Figure 9:
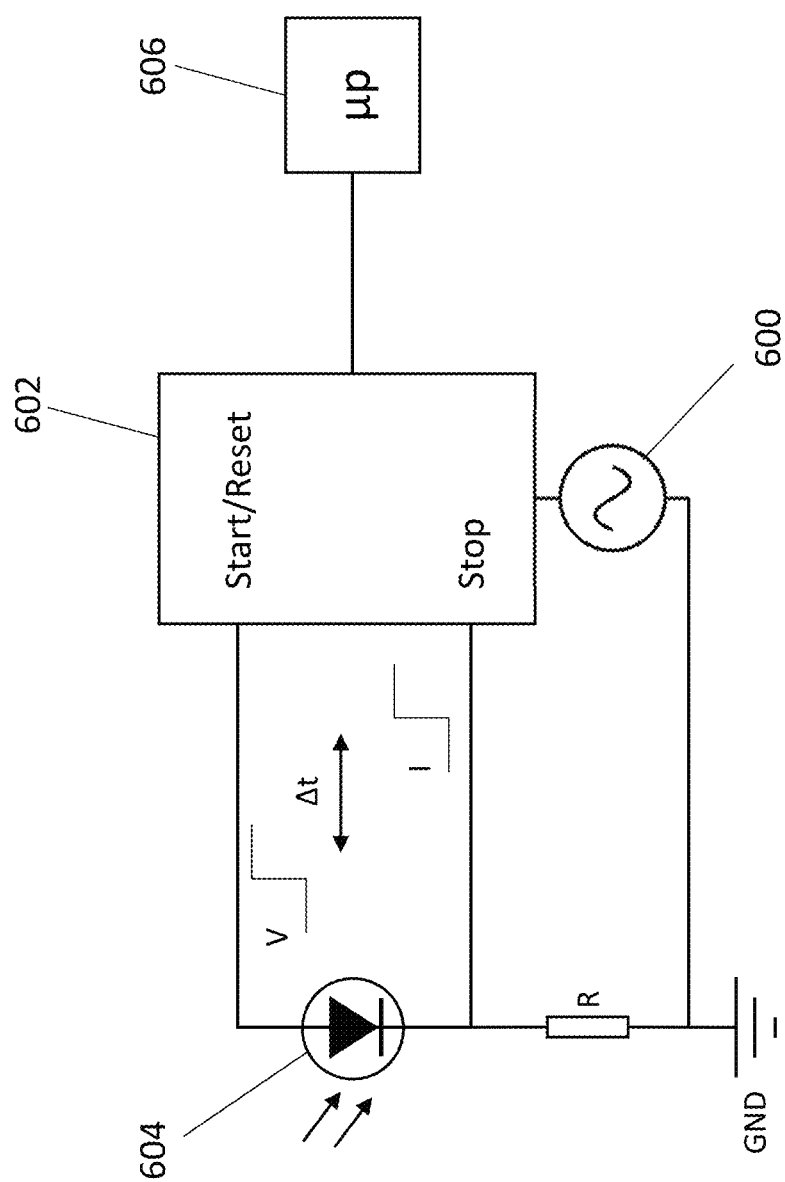
FIG. 9 illustrates a simplified circuit schematic for detecting light intensity at a forward biased photodiode.

In view of this, the intensity of an incident light at the photodiode can be measured by measuring the time delay between detecting the forward voltage VF and a measured current flow. An example circuit schematic for performing this detection is illustrated in FIG. 9. As seen therein, an oscillator 600 feeds a counter 602. A voltage applied at the photodiode 604 induces a current some time t later, which is measured as a voltage over the resistor, which in turn stops the counter 602. The counter 602 thus receives a start/reset signal together with a change in voltage of the photodiode 604 resulting in another voltage step stopping the counter again. Based on the frequency of the oscillator 600, the counter can then determine the time t until receiving a stop signal in the form of a forward current of the photodiode 604 as measured via the voltage over the resistor. The counter 602 output, a detected time t or signal corresponding to the detected time t, represents a light intensity of the incident light that can be processed by a microprocessor 606 or like circuitry. The microprocessor 606 may analyze the detected time t to identify an incident light intensity and further analyze the resulting PPG signal to determine a physiological parameter. Because the determination of incident light intensity utilizes just a counter 602, rather than the analysis of a small current induced by a greatly attenuated incident light, the corresponding circuitry for a forward biased photodiode has a lower peak current and energy consumption, and system complexity, than conventional PPG sensor systems requiring high powered light sources and amplification circuitry.

Moreover, if the light intensity at the photodetector is kept intentionally low (e.g., by using a lower powered light source), then the time delays are sufficiently long (e.g., μs to ms) so that the counter 602 does not need a special high frequency oscillator 600 as a time base. Instead, a relatively low frequency oscillator 600 already used in the hearing device (e.g., of only a few dozen MHz) can be sufficient to achieve a sufficiently high photodiode measurement resolution. Such lower frequency oscillators and their corresponding circuitry further limit power consumption and system complexity relative to higher frequency oscillators and associated circuitry. Still further, a weaker powered light source providing less light can be used with a sufficiently long light path to achieve an acceptable signal-to-noise ratio.

For example, a brightest intensity light at the photodetector might induce, for example, a 1 μs delay between the photodiode switching to its forward voltage, and a forward current flowing. Thus, with a 20 MHz oscillator, the counter 602 could determine the delay with 20 least significant bits (LSBs) and a 5% resolution. For darker conditions, when more blood blocks the light path, longer delays result and thus higher values are output by the counter 602. Preferably, the intensity of light emitted by the light source is weak enough to cause at least a 200 ns time delay, an even more preferably the delay is at least 1 μs. Thus, it is possible that no power consuming high frequency oscillator 600 is needed, and overall power for the PPG sensor can be further reduced. Power may still further be reduced by operating the light source, oscillator, and/or other related circuitry according to a duty cycle.

For even brighter conditions outside of operation, for example when the hearing device and PPG sensor are removed from the ear canal, an especially short time delay occurs that may not be detectable with the above-described low-frequency oscillator and counter. While such detection may not be suitable for determining a PPG signal, because the situation is a non-operating condition, the short delay may instead be used to detect that the hearing device has been or is being removed from the ear. Such a detection may cause the hearing device to e.g. automatically power down, or sound an alarm warning the user of a potential error or induce any other suitable measure.

In still further embodiments, the PPG sensor and hearing device may also comprise a motion sensor such as an accelerometer. Such a motion sensor can be used to detect sources of artifacts, which may then be removed from any resulting PPG signal during processing.

While various features are presented above, it should be understood that the features may be used singly or in any combination thereof. Further, it should be understood that variations and modifications may occur to those skilled in the art to which the claimed examples pertain. Accordingly, the above descriptions are merely exemplary and not intended to be limiting.

What is claimed is:

1. A hearing device comprising:
   a light source configured to emit light;
   a photodetector configured to detect the emitted light after interacting with tissue of a subject;
   a spout transparent to a wavelength of the emitted light;
   an audio receiver configured to deliver a sound to the subject through the spout; and
   a dome configured to conform to a shape of a subject's ear canal when the hearing device is in the ear canal,
   wherein the dome is configured to contact a tissue of the ear canal, and absorbs and/or reflects at least part of the emitted light such that an intensity of the emitted light at the wavelength passing through the dome is less than an intensity of the emitted light at the wavelength passing through the tissue, and
   wherein an output of the light source and an input of the photodetector are separated by the dome.

2. The hearing device of claim 1, wherein the light source comprises at least one light emitting diode.

3. The hearing device of claim 1, wherein the light source is configured to emit directional light toward a wall of the ear canal.

4. The hearing device of claim 1, wherein the light source is configured to emit diffuse light within the ear canal.

5. The hearing device of claim 1, wherein the output of the light source is located at the spout and the input of the photodetector is located at the receiver.

6. The hearing device of claim 1, wherein the output of the light source is located at the receiver and the input of the photodetector is located at the spout.

7. The hearing device of claim 1, wherein the spout comprises a light guide connected to the input of the photodetector.

8. The hearing device of claim 1, wherein the output of the light source is at a discrete location from the light source, the output of the light source being connected to the light source via a light guide.

9. The hearing device of claim 1, wherein the input of the photodetector is at a discrete location from the photodetector, the input of the photodetector being connected to the photodetector via a light guide.

10. The hearing device of claim 1,
    wherein the output of the light source is located at the spout and the input of the photodetector is located at the receiver,
    wherein the output of the light source is at a discrete location from the light source, the output of the light source being connected to the light source via a first light guide,
    wherein the input of the photodetector is at a discrete location from the photodetector, the input of the photodetector being connected to the photodetector via a second light guide.

11. The hearing device of claim 1,
    wherein the output of the light source is located at the receiver and the input of the photodetector is located at the spout, and
    wherein the dome is further opaque to ambient light.

12. The hearing device of claim 1, further comprising:
    a shield opaque to wavelengths of ambient and visible light, and configured to shield the photodetector from the wavelengths of ambient and visible light.

13. The hearing device of claim 1, wherein in the output of the light source and the input of the photodetector are at least at a 45° angle when viewed in a parasagittal cross-section of the ear canal.

14. The hearing device of claim 13, wherein the angle is acute relative to a posterior wall of the ear canal.

15. The hearing device of claim 1, wherein the light source is configured to emit light having a wavelength in the near infrared region.

16. The hearing device of claim 15, wherein the wavelength in the near infrared region is a first wavelength and the light source is configured to emit light having a second wavelength of about 660 nm.

17. The hearing device of claim 1,
    wherein the photodetector is a forward biased photodiode, and
    wherein the hearing device is configured to determine an intensity of light detected by the photodetector by measuring a time delay between an onset of a forward voltage of the photodetector and an onset of a forward current of the photodetector.

18. A hearing device, comprising:
    a light source configured to emit light;
    a photodetector configured to detect the emitted light after interacting with tissue of a subject;
    a spout;
    an audio receiver configured to deliver a sound to the subject through the spout; and
    a dome configured to conform to a shape of a subject's ear canal when the hearing device is in the ear canal,
    wherein the dome absorbs and/or reflects at least part of the emitted light,
    wherein an output of the light source and an input of the photodetector are separated by the dome,
    wherein the photodetector is a forward biased photodiode, and
    wherein the hearing device is configured to determine an intensity of light detected by the photodetector by measuring a time delay between an onset of a forward voltage of the photodetector and an onset of a forward current of the photodetector.

19. The hearing device of claim 18, wherein the light source is configured to emit light with a light intensity such that the time delay is at least 200 ns.

* * * * *